United States Patent [19]

Ohyama et al.

[11] Patent Number: 4,495,151
[45] Date of Patent: Jan. 22, 1985

[54] ELEMENT FOR IMMUNOASSAY

[75] Inventors: Kunio Ohyama; Nobuaki Nakagawa; Susumu Watanabe, all of Shizuoka, Japan

[73] Assignee: Toyo Jozo Kabushiki Kaisha, Shizuoka, Japan

[21] Appl. No.: 394,473

[22] Filed: Jul. 1, 1982

[30] Foreign Application Priority Data

Jul. 1, 1981 [JP] Japan ................ 56-101365

[51] Int. Cl.³ ............................................. G01N 33/54
[52] U.S. Cl. ........................... 422/102; 435/7; 435/296; 436/524; 436/810
[58] Field of Search ............... 435/7, 296; 436/807, 436/808, 810; 422/102

[56] References Cited

U.S. PATENT DOCUMENTS

| | | | |
|---|---|---|---|
| 4,135,884 | 1/1979 | Shen | 436/810 X |
| 4,197,287 | 4/1980 | Piasio | 436/807 X |
| 4,225,575 | 9/1980 | Piasio | 436/810 X |
| 4,305,924 | 12/1981 | Piasio | 436/810 X |

FOREIGN PATENT DOCUMENTS 2262479 6/1973 Fed. Rep. of Germany .
2418457 10/1979 France .

Primary Examiner—Sidney Marantz
Attorney, Agent, or Firm—Young & Thompson

[57] ABSTRACT

Apparatus for performing an immunoassay, comprises in combination a reaction tube closed at its bottom, and in the reaction tube a molded element having on its surface material having specific binding ability for a component in a liquid specimen to be assayed. The shape of the surface of the element adjacent the interior surface of the tube is the complement of the shape of the interior surface of the tube. A spacer rib is provided on the element, in contact with the interior surface of the tube. This rib holds the element in such position in the tube that the surfaces of complementary shape of the element and tube are shaped from each other a small but constant distance. A thin layer of constant thickness of a liquid specimen for immunoassay is thus receivable between the complementary surfaces. This arrangement increases the contact surface of the liquid medium in the reaction tube by the element, by establishing a homogeneous uniform layer of liquid medium. This avoids the need for stirring and shaking and reduces the required volume of the specimen to be assayed.

8 Claims, 11 Drawing Figures

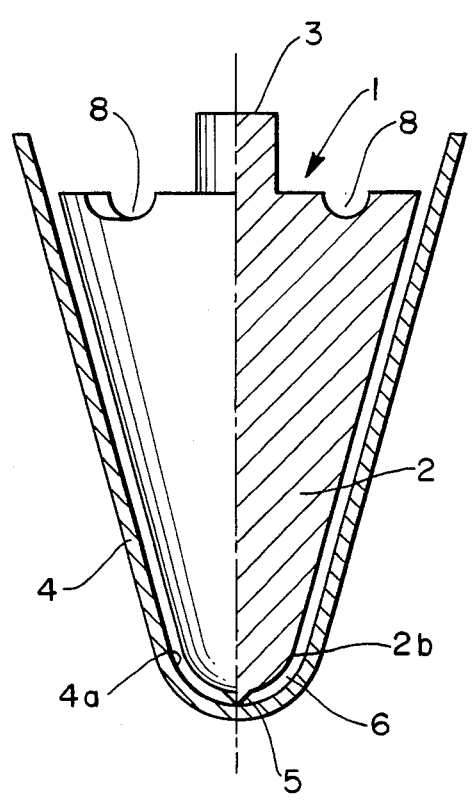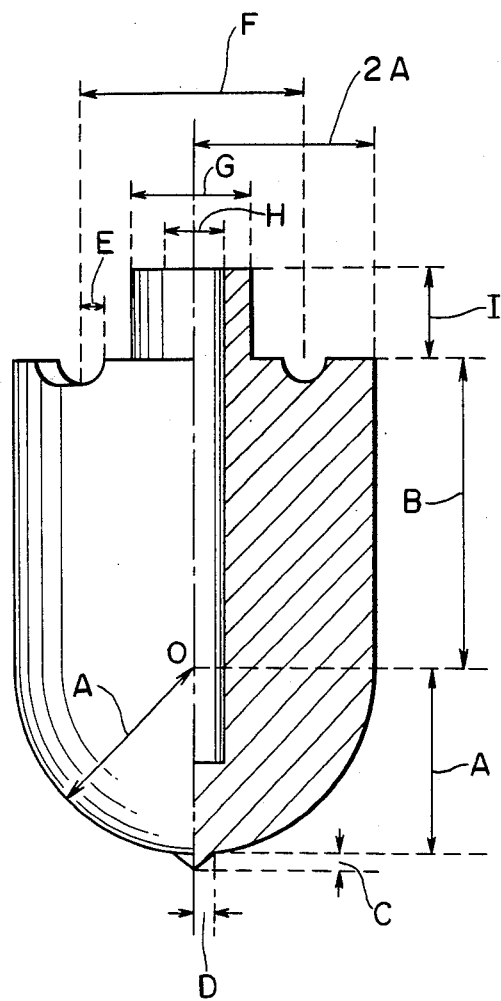
FIG. 4
FIG. 5

ELEMENT FOR IMMUNOASSAY

This invention relates to an element for immunoassay.

Quantitative assay methods of antigen-antibody reactions and analogous reactions are well known. These methods have been applied for quantitative and qualitative determination of trace components in body fluid such as blood and urine.

Examples of the trace components are, trace components in organisms, for example, physiologically active substances such as hormones, enzymes in organisms, administered drugs, specific antibodies against microorganisms and their metabolites, and the like.

These trace components are assayed by applying antigen-antibody reactions or analogous reactions, for example antibodies or receptors for hormones.

Assay methods applying the antigen-antibody reaction wherein antigen-antibody complex insolubles are precipitated, and a large number of antigen-antibody molecules aggregate, are already known as classical methods. Thesse are a method for directly measuring an amount of precipitate in a tube, immunodiffusion precipitating in a gel or a method using complement-fixation of an antigen-antibody complex. A method labelling a hapten, antigen or antibody and assaying the said labels is also well known. Among these methods, radioimmunoassay (RIA) is well known as a highly-sensitive assay method. However, in RIA the isotopes are dangerous.

Enzyme immunoassay (EIA), in which enzyme labelling is used instead of radioisotope labelling, has recently been used.

The principle of EIA is an enzyme is bound with a drug, an antigen including hapten (hereinafter called inclusively as antigen) or antibody, and the degree of antigen-antibody reaction is estimated by measuring the said enzyme activity, then the amount of antigen or antibody can be measured.

Embodiments of these enzyme immunoassays are that the object to be assayed is an antigen or antibody; an enzyme labelled antigen or antibody, or a non-labelled antigen or antibody is either competitive or non-competitive; or the complex is separated or not separated during the competitive reaction. Furthermore the sandwich method can be mentioned.

An element for immunoassay of the present invention is used for the competitive reaction method and sandwich method, most preferably a method using an insoluble carrier element for immunoassay and immobilized antigen or antibody.

In the prior known immunoassay using an insoluble carrier, polystyrene or glass beads or paper disc carriers are used. Or the inner wall of the reaction tube is used for the carrier itself. These prior known methods have a number of disadvantages, for example, requiring a large amount of medium for the immune reaction, lowering the rate of immune reaction and suffering a non-homogeneous concentration during the reaction. In order to avoid these disadvantages, operations such as stirring or shaking the reaction mixture or tube are essentially required. Therefore, only a relatively high concentration of the substance can be measured.

A principal object of the present invention is to provide an element for immunoassay which comprises an element of insoluble carrier molded in the specific structure, increasing the contacting surface in the reaction tube by the said element, thereby holding the said contacting surface of the reaction mixture as a homogeneous uniform layer and avoiding complex operations such as stirring and shaking.

A further object of the present invention is to provide an element for immunoassay which can perform immunoassay with a small amount of immune reaction medium and under homogeneous and rapid conditions.

The figures of the accompanying drawings show the preferred embodiments of the present invention, and in the figures.

Figure 6:
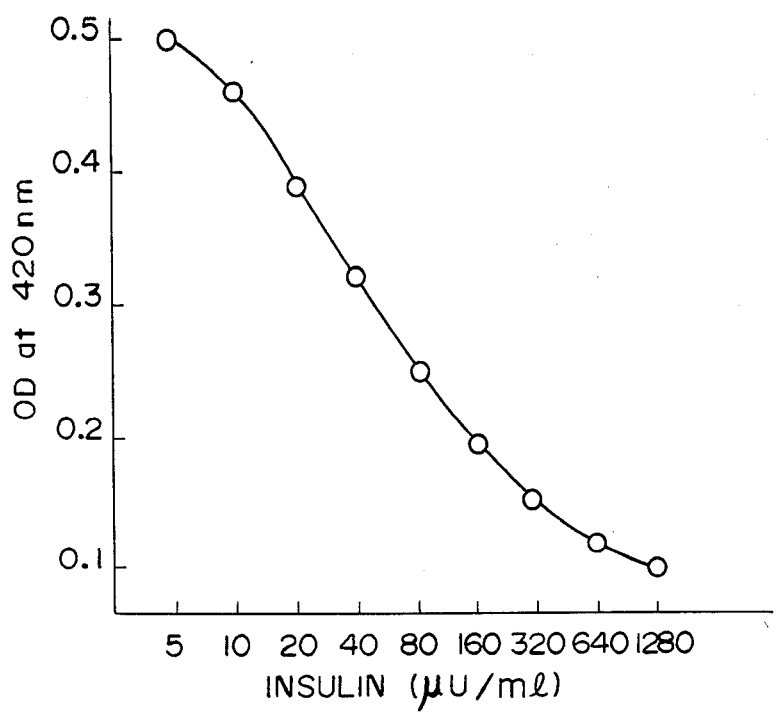
Figure 7:
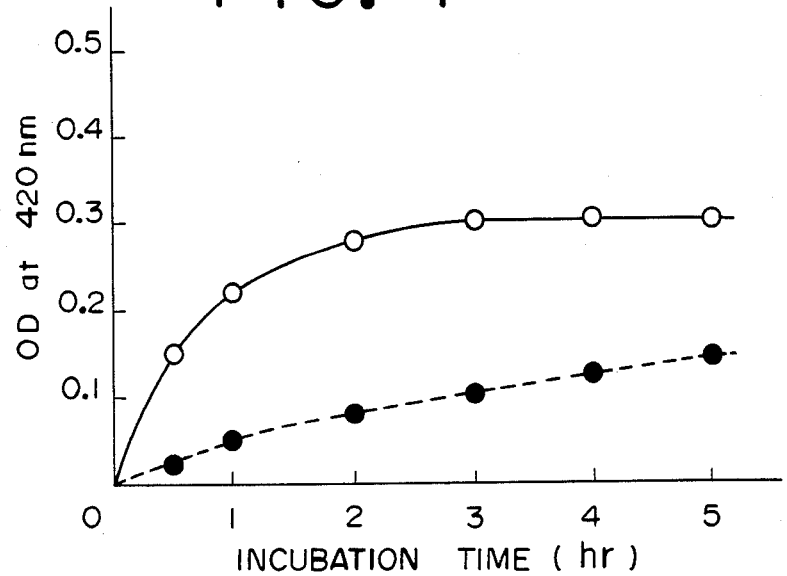
Figure 8:
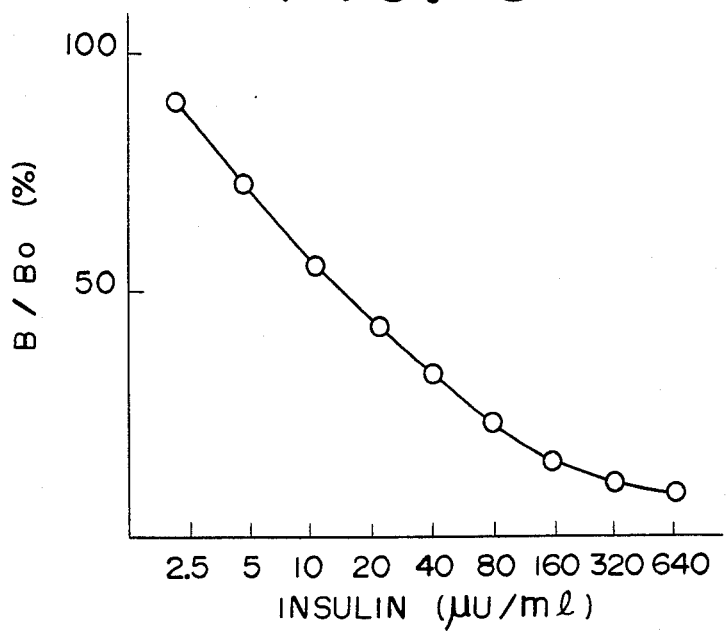

FIGS. 3($a$), ($b$) and ($c$) are plan views of different embodiments of the cut groove of the upper part of the element;

FIG. 4 is an enlarged sectional view of the element exemplified in Example 2;

FIG. 5 is a dimensioned view for production of the element;

FIG. 6 is the quantitative assay curve of insulin by EIA;

FIG. 7 shows the comparative data of EIA by the present invention and by prior known beads;

FIG. 8 is the quantitative assay curve of insulin by RIA; and

Figure 9:
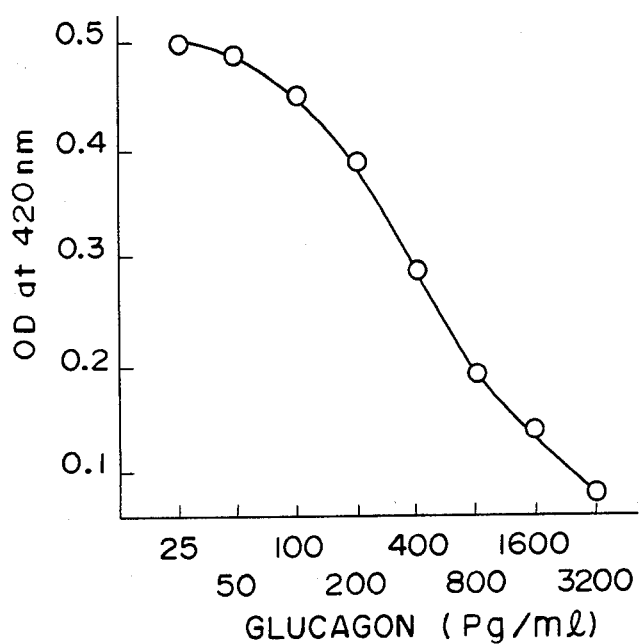

FIG. 9 is the quantitative assay curve of glucagon by EIA.

In the figures, the reference numerals designate 1: element for assay; 2: element proper; 4: reaction tube; 5: spine; 6: gap; and 8: cut groove.

The element of the present invention can be used for either EIA or RIA, by the competitive assay method or the sandwich method or the solid phase method.

Embodiments of the insoluble carrier are the insoluble carriers conventionally used in EIA or RIA. In the immobilization of antibodies, the substance to be bound in general is an antigen protein, and hence the carriers used in the production of immobilized protein can be used. Examples of the said insoluble carrier are insoluble protein carriers such as albumin or gelatin treated with glutaraldehyde; insoluble semisynthetic polymer carriers such as a polysaccharide which is prepared from epichlorohydrin treatment or bromcyanide treatment and amination treatment of agarose, cellulose or dextrin; an aminated polymer or copolymer of acrylonitrile, acrylic acid, acrylic acid ester, methacrylic acid, methylmethacrylic acid, vinyl alcohol, vinyl acetate, styrene, aminostyrene, divinylbenzene, acrylamide ethylene, maleic anhydride and crotonic acid (polymer resin); and insoluble inorganic carrier such as an aminated silane compound.

Introduction of amino group into the said insoluble carrier is performed by any conventional method, for example amination by reduction of nitrile group, aminoalkylation of hydroxy group by γ-aminopropyltriethoxysilane, conversion of hydroxymethyl group to aldehyde group by periodate oxidation and amination of the said aldehyde group by diamine, conversion of polysaccharide hydroxy group to imidocarbonate group by bromcyanide, converting amido group to iminohalogenide group by phosphorus halogenide, and introduction of a new functional group by use of a functional group introduction reagent.

Preferred examples of insoluble carrier are polymer resins such as nylon, polystyrene, polyacrylamide and vinyl chloride, insoluble polysaccharides such as cellulose or dextran, and inorganic materials such as glass.

The shape of the element is optionally a ball-shaped or spearhead-shaped or the like shape, or alternatively it is solid mold, such as metals and plastics, covered to form the shape of the element.

An embodiment of the element for immunoassay of the present invention is explained with reference to the figures as follows.

Figure 1:
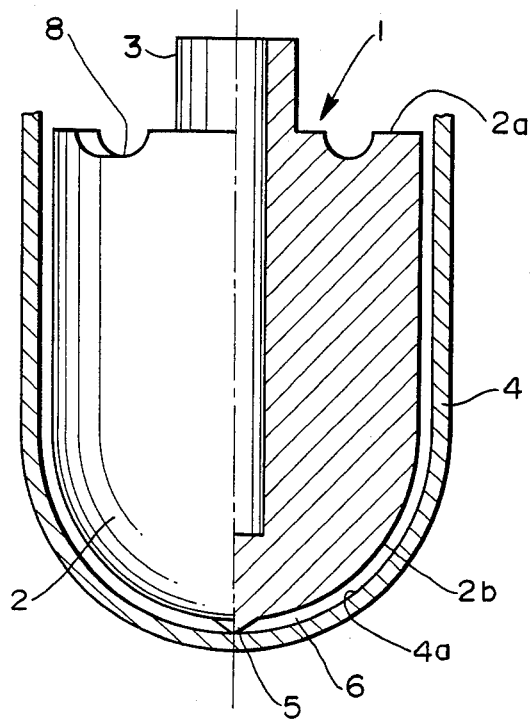
FIG. 1 is an enlarged sectional view of the element exemplified in Example 1.

FIG. 1 is an overall illustration of the element 1. An element 1, which consists of, for example, polymer resin material such as nylon, comprises element proper 2 and a joint mount 3 which projects centrally from the upper part 2a of the said element proper 2. A joint mount 3 is joined to an operation bar (not shown), however said joint mount 3 itself is optionally elongated to form the operation bar. Element proper 2 is molded in a ball-shape and its outer diameter is spaced by a narrow gap from the inner diameter of the reaction tube 4. The top of the lower part of the element proper 2 has a wedge-shaped spine 5, and a constant gap 6 is held by the said spine between outer arcuate surface 2b of the element proper 2 and inner arcuate surface 4a of the reaction tube 4. The said spine can be a convex shaped spine instead of the wedge-shaped spine. In general the constant gap is to be held by the said spine 5. The height of the spine is to be kept constant in order to hold a constant gap between the element proper 2 and inner surface of reaction tube 4. At the upper part 2a of the element proper 2 is cut the groove 8, with a square shape, centering around the joint mount 3. The edges of the cut groove 8 open on the periphery of the element proper 2, and the surface tension of the reaction mixture at the periphery of the upper part 2a is thereby weakened. The shapes of the groove 8 are optionally semicircular, elliptical, trapezoidal, triangular, quardrilateral, and the like.

An element for immunoassay of the present invention has the shape hereinabove illustrated, and when the said element is immersed into the reaction mixture in the reaction tube, the wedge-shaped spine of the element touches the inner base of the tube to form the narrow gap between the outer surface of the element and inner surface of the reaction tube (refer to FIG. 1). Hence, if the amount of reaction mixture is small, the said reaction mixture is guided up into the gap by means of inserting the element, and the reaction mixture fills up to the top edge of the element and overflows through the cut groove to lose its surface tension. Therefore the reaction mixture is held at the outer surface of the element under constant conditions (constant thickness of the layer).

Figure 3A:
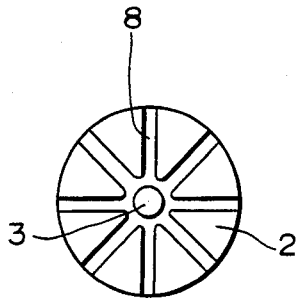
Figure 3B:
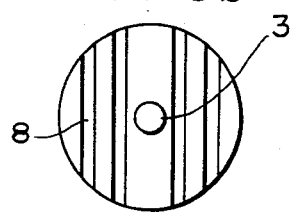
Figure 2:
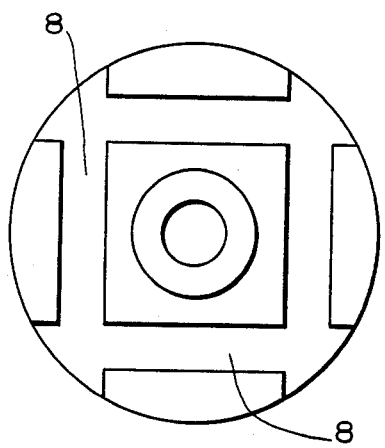
FIG. 2 is a plan view thereof.
Figure 3C:
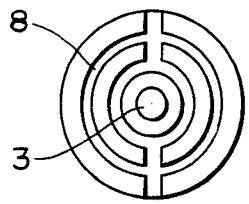

Modified embodiments of the said cut groove 8 are as shown in FIG. 3. In FIG. 3(a) is shown a radial arrangement. In FIG. 3(b) is shown parallel grooves. Further, in FIG. 3(c) is shown circular and radial grooves. Other modifications of the cut groove 8 opening through the periphery of the upper part 2a can be used.

Another modified embodiment of the element 1 is shown in FIG. 4. In the said embodiment, the element proper 2 is molded in a spearhead shape. Hence the shape of reaction tube 4 has a taper corresponding to the shape of the element proper 2. The shapes of the element can be modified according to the shapes of the commercially available test tubes. The structural features of the element proper 2 are the same as illustrated in FIG. 1 so that the parts of the elements are indicated by the same numbers, and the explanation is omitted.

The antigen, antibody or receptor for the drugs is conjugated to the element by the conventional chemical or physical means to prepare a solid phase insoluble-antigen, -antibody or -receptor.

The solid phase can be prepared by introducing functional groups for conjugating antibodies, etc. to the above insoluble carrier, then molding the specific shape, or by introducing the functional groups after molding the element shape. For example, nylon 66 is molded previously to the shape of the element, thereafter activated by dimethyl sulfate or imidechloride, then treated with hexamethylenediamine or glutaraldehyde to conjugate the antibody such as a secondary antibody, which is further bound with a primary antibody by an immune reaction. Dextran gel such as Sephadex is also molded to the shape of the element, activated with bromcyan (BrCN) and conjugated with an antibody to prepare the immobilized antibody. Polystyrene is previously molded, thereafter chemically treated with sulfuric acid or physically adsorbed to prepare an immobilized antibody, etc. Glass is aminoalkylsilylated with an amino group introducing reagent such as $\gamma$-aminoalkyltriethoxy silane, and the said amino group is conjugated by the conventional immobilized method. In general, any chemical immobilization method, and any polyfunctional compound, which can conjugate the functional group or functional group introduced into the molecule of the insoluble carrier and the functional group in the antigen molecule such as amino-, hydroxy-, carboxy-, thiol- or aldehyde-group, can be used. Examples of the prior known polyfunctional compound are reactive derivatives, for example, diisocyanate such as hexamethylenediisocyanate or 2,4-toluene diisocyanate, diisothiocyanate such as hexamethylenediisothiocyanate, dialdehyde such as succinaldehyde or glutaraldehyde, sulfidocarboxylic acids such as N,N'-ehtylenebis-maleimide, N,N'-O-phenylenedimaleimide, bis-diazobenzidine, N,N'-polymethylenebisiodoacetamide, dimethylmalonimidate, dimethyladipinimidate, 3-(2'-benzothiazolyl-dithio)-propionate, 3-(2'-pyridyl-N-oxide-dithio)propionate or 6-N[3-(2'-benzothiazolyldithio)propionyl]caproate, or succinimide ester, p-nitrophenyl ester, acid chloride or imidate thereof (Japan. Pat. Appln. No. 53-85900), and maleimide carboxylic acid such as maleimide benzoic acid, maleimide phenylacetic acid or maleimidephenylpropionic acid, or a reactive derivative thereof.

Also the polyfunctional compound can be used for introducing reagents which can introduce functional groups into insoluble carrier.

The solid phase can be prepared by reacting the insoluble carrier with the functional compound in an inert medium such as buffer solution at pH 6–8 or acetone, methanol, ethanol, dioxane, dimethylsulfoxide, dimethylacetamide or tetrahydrofuran, or a mixture thereof, at room temperature or under cooling. Thereafter, if required, the insoluble carrier is washed, added to the same inert medium, then antibodies or the like are added to react with the insoluble carrier.

A conjugated element surface-secondary antibody-primary antibody can be prepared, at first, by conjugating the secondary antibody on the molded element, thereafter binding with the primary antibody. The said element is preferred because of not denaturing the immune activity of the primary antibody. Conventional EIA or RIA technique can be used for binding the enzyme with antibody, antigen or hapten. Prior known conventional enzymes such as oxide-reductase, hydrolase, transferase, lyase, isomerase, or ligase can be used as the labelling enzyme.

Compounds to be assayed such as antigens and antibodies be assayed by using the element for assay of the present invention by means of conventional EIA or RIA.

An embodiment of the element adapted for a test tube 15×105 mm (inner diameter; 12.8 mm±0.1 mm) is shown in FIG. 5. In the Figure; A: semispheric part, radius 6 mm, B: column, height 10 mm, C: conical spine, height 0.4 mm, D: radius of conical spine 0.5 mm, E: semispherical groove, radius 0.75 mm, F: length between centers of opposite grooves 7.5 mm, G: diameter of convex part joined with operation bar, 4 mm, and H: diameter of joint hole of the convex part for setting the operation bar, 2 mm, I: height of convex part, 3 mm. In the case of the said element, wherein the size of the column part is height: 10 mm, diameter: 12 mm and semispheric part is radius 6 mm, the amount of buffer of the immune reaction is 100 µl, and is a solution which contains a component bound with a labelling compound 100 µl and the specimen (serum or urine) is 100 µl. Under these conditions, constant thickness of the reaction liquid layer 0.4 mm can be kept. The reaction time can be varied depending upon the object to be assayed, and is at 37° C. 1–5 hours for insulin, and at 5° C. 8–48 hours for glucagon. Optional temperatures and times can be selected according to the component to be assayed, furthermore the amount of liquid is controlled according to the size of the element.

Embodiment of the insulin assay in serum is as follows.

The element hereinabove is inserted in the test tube (15×105 mm, inner diameter 12.8 mm±0.1 mm) containing buffer 100 µl, enzyme labelled insulin solution 100 µl and solution containing an aliquot concentration of insulin, and the mixture is incubated at 37° C. for 3–4 hours. Distilled water or physiological saline (5 ml) is added in the tube to wash the element, then it is inserted into the test tube which previously contains substrate solution (400–500 µl), and the mixture is incubated at 37° C. for 10–60 min. A reaction stopper solution (2.1–2.0 ml) is added therein and the element is removed, then consumed or liberated components are assayed by conventional enzyme immunoassay, for example absorbancy. The amount of insulin is calculated from a standard curve.

A detailed embodiment is as follows.

6,6-nylon is molded as the shape of element shown in FIG. 5 (hereinafter designated 6,6-nylon element), activated by the imidechloride method using phosphorus pentachloride and treated with hexamethylenediamine and glutaraldehyde to obtain the required 6,6-nylon element. IgG is conjugated with the said element by reacting with the IgG fraction of rabbit anti-guinea-pig IgG serum to obtain immobilized IgG. Guinea-pig antiinsulin serum is reacted with the immobilized IgG to obtain 6,6-nylon element-anti-guinea pig IgG-insulin antibody (hereinafter designates as immobilized antibody). The immobilized antibody is reacted with β-galactosidase-bound insulin and various concentrations of standard insulin. After washing, β-galactosidase activity of the immobilized antibody is assayed to prepare the standard curve. Furthermore, an aliquot amount of serum specimen is added instead of the standard insulin to calculate the insulin content in the specimen as compared with standard curve.

As hereinabove explained the element for assay of the present invention is advantageously and preferably useful for immune reaction assay without stirring and shaking operations and with a small amount of samples for only a short time.

The following examples illustrate the assay method of the present invention but are not to be construed as limiting the invention to the said examples.

EXAMPLE 1

Assay method of insulin

[Preparation of immobilized antibody]-I:

Fifty 6,6-nylon elements of the size and shape as shown in FIG. 5 were stirred with phosphorus pentachloride (4 g) and pyridine (4 g) in benzene (60 ml) for 2 days and washed four times with benzene to obtain imidechloride of 6,6-nylon elements. An aqueous solution (pH 11.5, 50 ml) containing 100 mM hexamethylenediamine was added to the element, reacted at room temperature for one hour, washed with 0.1M phosphate buffer (pH 8.0), a 0.1M phosphate buffer solution (pH 8.0, 50 ml) of 4% glutaraldehyde was added thereto and the mixture was reacted at room temperature for one hour. The elements were washed with 0.1M phosphate buffer (pH 8.0). Spacer and 6,6-nylon elements (50 elements) were added in the 0.1M phosphate buffer (pH 8.0, 50 ml) containing IgG fraction (5 ml) of rabbit anti-guinea pig IgG serum, and the material was reacted at 5° C. overnight to obtain the elements in which immobilized IgG 50 µg was present on each functional element. [anti-guinea pig IgG activity/element=600−700 ng antibody activity (titer)].

Serum containing insulin antibody [23200 dilution, diluted with a solution (50 ml) of 0.25% BSA, 5 mM EDTA, 3 mM MgCl$_2$, 0.15M NaCl, 0.1% NaN$_3$ in 0.01M phosphate buffer (pH 7.4)] (250 ng insulin antibody) was added to the element and the material was incubated at 5° C. overnight to obtain the conjugate (nylon element-anti-guinea pig IgG-insulin antibody). Insulin antibody activity (titer) was insulin antibody titer 4.5±0.2 ng/element assayed by insulin-β-galactosidase conjugate.

[Preparation of immobilized antibody]-II:

Fifty 6,6-nylon elements were added to a methanol solution (50 ml) of 30% v/v dimethyl sulfate, and the material was reacted at 37° C. for 50 minutes, washed with methanol and 100 mM aqueous hexamethylenediamine (pH 11.5, 50 ml) was added thereto. The mixture was reacted at room temperature for 1 hour and washed with 0.1M phosphate buffer (pH 8.0). 4% v/v glutaraldehyde in 0.1M phosphate buffer (pH 8.0, 50 ml) was added thereto, and the material was reacted at room temperature for 1 hour and washed with 0.1M phosphate buffer (pH 8.0) to introduce the spacer into 6,6-nylon element. [nylon element-anti-guinea pig IgG-insulin antibody] was prepared according to the same procedure in the [Preparation-I].

[Preparation of immobilized antibody]-III:

Fifty polystyrene elements were added to IgG fraction (50 µg) of anti-insulin guinea pig serum in 0.1M phosphate buffer (pH 8.0) and the material was reacted at 5° C. overnight to obtain [polystyrene element-insulin antibody] conjugate. [40±0.38 ng insulin antibody titer/element].

[Preparation of β-galactosidase-insulin]:

3-(benzothiazol-2'-yl-dithio) propionic acid succinimide ester (6.5 mg) in dimethylformamide solution (1.7 ml) was added to insulin (60 mg) dissolved in 0.1M phosphate buffer (pH 8.0)(17 ml), the mixture was reacted for 1 hour under cooling and adjusted to pH 5.0 to collect the precipitate. The precipitate was dissolved in 0.1M phosphate buffer (pH 7.0, 40 ml)(8.9 mg/ml insulin). The solution (10.0 µl) was added to β-galactosidase (6 mg), and the mixture was reacted for 1 hour. The reaction mixture was passed through a column (1.5×120 cm) of Sephadex G-100 and eluted with 0.15M NaCl containing phosphate buffer (pH 7.4) to collect the fraction of 65-73 ml. The said fraction contained insulin-β-galactosidase conjugate, wherein the amino group of insulin was bound with the thiol group of β-galactosidase, abbreviated as (insulin)-CO-(CH$_2$)$_3$-S-(β-galactosidase). (insulin 2.4 µg/ml, conjugate of one mole of β-galactosidase in one mole of insulin, 95% activity of insulin conjugate for insulin antibodies.

[Preparation of I$^{125}$-insulin]:

I$^{125}$-insulin was prepared according to the method described by W. M. Hunter and F. C. Greenwood [Nature, 194, 495 (1962)]. BF separation was performed with a Sephadex G-25 column (0.9×20 cm).

[EIA of insulin]:

A buffer solution for immune reaction [0.25% BSA, 5 mM EDTA, 3 mM MgCl$_2$. 0.15M NaCl, 0.1% NaN$_3$ in 0.01M phosphate buffer (pH 7.4), 100 µl], β-galactosidase-insulin conjugate (200 pg insulin, 100 µl) and insulin standard solution (5-1280 µU/ml, 100 µl) were introduced in a small test tube (15×105 mm, inner diameter 12.8±0.1 mm). An anti-insulin immobilized element prepared as above [Preparation-II] was introduced therein and the material was incubated at 37° C. for 3-4 hours. Distilled water or physiological saline (5 ml) was added thereto and the element was taken out with washing. The said element was introduced into a small test tube containing solution for assaying β-galactosidase activity (500 µl)[0.1% BSA containing o-nitrophenol-β-D-galactopyranoside 5 mg/ml, 0.15M NaCl, 1 mM MgCl$_2$, 0.1% NaN$_3$ ] in 10 mM phosphate buffer (pH 6.7) 85 parts and 200 mM mercaptoethanol in methanol 15 parts] and the material was incubated at 37° C. for 1 hour. Reaction stopper [100 mM glycine-NaOH buffer (pH 11.5), 2 ml] was added, the element was removed and the absorbancy was measured at 420 nm.

The result is shown in FIG. 6, in which the insulin assay system of the present invention shows the preferred quantitative curve.

In the assay of insulin in specimens (serum, plasma, etc.), standard insulin solution (100 µl) was replaced by a specimen (100 µl) and assayed according to the same operation as hereinabove illustrated.

At 40 µU/ml of insulin in the specimen, the above anti-insulin immobilized element (II) and prior known conventional immobilized beads (8 beads; 6,6-nylon, diameter 4.5 mm, anti-insulin immobilized beads prepared by the same procedure as in the preparation of anti-insulin immobilized element hereinabove II, 8 beads were required for the same surface area) were compared for reaction time and conjugation ratio. The results are shown in FIG. 7, In the Figure, o———o: element of the present invention •-----•: prior known beads.

[RIA of insulin]:

A buffer solution for an immune reaction [the same as above] (100 µl), I$^{125}$-insulin (insulin 100 pg)100 µl) and insulin standard solution (2.5-640 µU/ml, 100 µl) were introduced into a small test tube (15×105 mm, inner diameter 12.8±0.1 mm). An anti-insulin assay element was introduced therein and the material was incubated at 37° C. for 3-4 hours. Distilled water or physiological saline (5 ml) was added. The element was taken out with washing. The element was transferred to the another test tube and the radioactivity was measured. The results are shown in FIG. 8, which shoes the high quality of the quantitatige curve.

In FIG. 6: X-axis: insulin concentration, $$Y\text{-axis: } B/Bo\ (\%) = \frac{X\text{-axis insulin counts}}{\text{control (no insulin) counts}} \times 100$$

EXAMPLE 2

Assay method of glucagon

[Preparation of immobilized antibody]:

Fifty γ-aminopropyl triethoxysilane treated glass elements were added to 2% glutaraldehyde in 0.1M phosphate buffer (pH 8.0, 50 ml), and the material was reacted at room temperature for 1 hour, and washed with 0.1M phosphate buffer (pH 8.0). A 0.1M phosphate buffer (pH 8.0, 50 ml) containing IgG fraction (5 mg) of anti-rabbit IgG serum (goat) was added and the material was reacted at 5° C. overnight to obtain immobilized IgG (80 µg) elements. [anti-rabbit IgG activity (titer): 900-1000 ng/element].

Anti (16-19)glucagon fragment serum (rabbit)(15000 dilution with immune reaction buffer hereinabove)(50 ml)[anti-(16-29)glucagon fragment: 68 ng] was added to the said elements, and the material was reacted at 5° C. overnight to obtain [element-anti-rabbit IgG-anti-(16-29)glucagon fragment]. [1.1±0.05 ng, anti-(16-29)-glucagon fragment activity assayed by (16-29)glucagon fragment-β-galactosidase conjugate].

[Preparation of (19-29)glucagon ·fragment-β-galactosidase]:

100 mM EDTA (10 µl) and 0.1% 3-(2'-benzothiazolyl-dithio) propionic acid succinimide ester in dimethylformamide (625 µl) were added to (19-29)glucagon fragment (0.4 mg) dissolved in 50 mM phosphate buffer (pH 8.0, 0.4 ml). The reaction mixture was passed through a column (1.5×40 cm) of Sephadex G-15 to collect the passed solution which contained a derivative of 3-(2'-benzothiazolyl-dithio)propionyl group introduced at the n-terminal of the (19-29)glucagon fragment. The said derivative (20 µg) in 50 mM phosphate buffer (pH 7.0, 2 ml) was added to β-galactosidase (6.19 mg) in 50 mM phosphate buffer (pH 7.0) and reacted at room temperature for 1 hour. The reactions mixture was passed through a column (1.5×90 cm) of Sephadex G-150 and the passed solution was collected to obtain β-galactosidase-(19-29)glucagon fragment conjugate (purity: 95%) [N-terminal of (19-29)glucagon fragment was bound to thiol group of β-galactosidase].

[EIA of glucagon]:

A buffer solution for immune reaction [0.25% BSA, 5 mM EDTA, 3 mM MgCl$_2$, 0.15M NaCl, 0.1% NaN$_3$ in 28 mM Veronal buffer (pH 7.4) 100 µl], β-galactosidase-(19-29)glucagon fragment (glucagon fragment 45 pg)(100 µl) and glucagon standard solution (25-3200 pg/ml)(100 µl) were introduced in a small test tube (15×105 mm, inner diameter 12.8±0.1 mm). An anti- (16-29)glucagon fragment assay element was added therein and reacted at 5° C. for 1-2 nights. The element was taken out with washing by addition of distilled water or physiological saline (5 ml). The element was introduced into another test tube containing the β-galactosidase activity assay solution hereinbefore (500 μl) and the material was incubated at 37 ° C. for 2.5 hours. The same reaction stopper solutions hereinbefore (2 ml) were added and the absorbancy of supernatant solution was measured at 420 nm.

The results are shown in FIG. 9, which shows the excellent quantitative curve for a glucagon assay system.

What we claim is:

1. In apparatus for performing an immunoassay, comprising in combination a reaction tube closed at its bottom, and in the reaction tube a molded element having on its surface material having specific binding ability for a component in a liquid specimen to be assayed; the improvement in which the shape of the surface of the element adjacent the interior surface of the tube is the complement of the shape of the interior surface of the tube, and spacer means on the element in contact with the interior surface of the tube, said spacer means holding the element in such position in the tube that said surfaces of complementary shape are spaced from each other a small but constant distance thereby to receive between said surfaces of complementary shape a thin layer of constant thickness of a liquid specimen for immunoassay.

2. Apparatus as claimed in claim 1, in which said component to be assayed is an antibody and said material is an antigen.

3. Apparatus as claimed in claim 1, in which said component to be assayed is an antigen and said material is an antibody.

4. Apparatus as claimed in claim 1, in which said component to be assayed is a hormone or drug hapten and said material is a receptor thereof.

5. Apparatus as claimed in claim 1, in which said shape of the surface of the lower part of the element is semi-spherical.

6. Apparatus as claimed in claim 1, in which said shape of the surface of the element is a rounded spearhead shape.

7. Apparatus as claimed in claim 1, in which said spacer means comprises a rib on said element.

8. Apparatus as claimed in claim 1, and upwardly opening grooves in the upper surface of said element, said grooves opening through the edges of said element.

* * * * *